United States Patent [19]

Todd, III et al.

[11] Patent Number: 4,935,234

[45] Date of Patent: * Jun. 19, 1990

[54] METHOD OF REDUCING TISSUE DAMAGE AT AN INFLAMMATORY SITE USING A MONOCLONAL ANTIBODY

[75] Inventors: Robert F. Todd, III; Paul J. Simpson; Benedict R. Lucchesi, all of Ann Arbor, Mich.; Stuart F. Scholossman, Newton Centre; James D. Griffin, Sherborn, both of Mass.

[73] Assignee: Dana-Farber Cancer Institute, Boston, Mass.

[*] Notice: The portion of the term of this patent subsequent to Jun. 20, 2006 has been disclaimed.

[21] Appl. No.: 165,025

[22] Filed: Mar. 7, 1988

Related U.S. Application Data

[63] Continuation-in-part of Ser. No. 61,336, Jun. 11, 1987, Pat. No. 4,840,793.

[51] Int. Cl.$^5$ .................... A61K 39/395; C07K 15/28; C12P 21/08

[52] U.S. Cl. .................... 424/85.8; 530/387; 530/388; 530/806; 530/808; 435/240.27

[58] Field of Search ............... 424/85.8; 530/387, 808, 530/382, 828; 435/240.27

Primary Examiner—Garnette Draper
Assistant Examiner—Jeff Kushan
Attorney, Agent, or Firm—Myron C. Cass

[57] ABSTRACT

A method of reducing tissue injury in humans or other animal species using a monoclonal antibody to inhibit specific phagocyte functions. The monoclonal antibody is selected to bind to phagocytic leukocytes for the purpose of inhibiting migration to an inflammatory site in the body and to inhibit the adhesion and spreading of activated leukocytes reaching such an area and then, block release of toxic substances by these cells. The monoclonal antibody is administered in vivo prior or early in the course of an experience leading to an injurious inflammatory response such as can result from restoration of myocardial blood flow interrupted by an acute coronary thrombosis.

10 Claims, 2 Drawing Sheets

METHOD OF REDUCING TISSUE DAMAGE AT AN INFLAMMATORY SITE USING A MONOCLONAL ANTIBODY

RELATED APPLICATION

This application is a continuation-in-part of U.S. Ser. No. 07/061,336, filed June 11, 1987 now U.S. Pat. No. 4,840,793, and entitled METHOD OF REDUCING TISSUE DAMAGE AT AN INFLAMMATORY SITE USING A MONOCLONAL ANTIBODY.

This invention relates to a novel method of reducing tissue damage mediated by inflammatory leukocyte activation by administering in vivo a monoclonal antibody specific for leukocyte adhesion-promoting molecules. More particularly, substantial reduction in the inflammatory response of leukocytes to inflammatory signals resulting in damage to tissue or other parts of a human body is achieved by administering in vivo a select monoclonal antibody that binds to a surface determinant expressed by granulocytes and mononuclear phagocytes of human or animal origin whereby to specifically inhibit certain adhesion-dependent leukocyte functions which contribute to tissue injury especially, but not limited to, in a myocardial infarct experience.

BACKGROUND OF THE INVENTION

Peripheral blood in the circulatory system of a human or animal is comprised principally of red blood cells, i.e. erythrocytes, and white blood cells, i.e. leukocytes. The variety of functions of leukocytes and their clinical relevance has generated great interest in the scientific community. The family of white blood cells is comprised of neutrophils, monocytes, eosinophils, basophils and lymphocytes. Lymphocytes are of T-lymphocyte and B-lymphocyte types which have numerous subsets. Neutrophils, eosinophils and basophils are known as "granulocytes" because of their content of cytoplasmic granules.

Neutrophils, monocytes, eosinophils and basophils are known as phagocytes because their primary function in the human immune system is to phagocytize or ingest bacteria, microorganisms and other types of foreign materials. These cells are produced from common progenitor cells in the bone marrow of a human or animal and are known to circulate in peripheral blood and finally, enter tissues as necessary for control of infection or to participate in any type of inflammatory reaction. However, each of these phagocytes has different functions and behaves as a related but separate system.

The neutrophil is the most common leukocyte in human and animal peripheral blood. One microliter of normal human whole blood includes, on average $5 \times 10^3$ leukocytes of which 3,075 are neutrophils, 150 are eosinophils, 25 are basophils, 250 are monocytes, and 1,500 are lymphocytes.

In the response of granulocytes or mononuclear phagocytes to any type of infection or inflammation, these cells are activated first to migrate to the appropriate area in response to chemo-attractant factors, such as, certain bacterial products, complement component, and other factors. This attraction process is termed "chemotaxis". Once in an area of inflammation or infection, granulocytes and mononuclear phagocytes must establish a firm attachment to their targets. For this purpose, these cells possess a number of specific cell surface receptor glycoproteins that promote this interaction, such as complement, Fc, and fibronectin receptors.

A very important family of cell surface receptor glycoproteins is the leukocyte cell adhesion molecule (LEUCAM) family (CD11/CD18). This family is comprised of at least three(3) cell surface proteins which have two (2) subunits each. They share a common beta subunit of 94,000 dalton molecular weight (CD18), and have different alpha subunits. The known members of this family are termed LFA-1 (CD11a/CD18), Mo1 (CD11b/CD18), and P150,94 (CD11c/CD18) which evidence alpha subunits of 180,000, 155,000 and 150,000 dalton molecular weight, respectively. Each of these cell surface proteins has been specifically identified through the use of monoclonal antibodies. The biological importance of this family of surface glycoproteins has been recognized through the identification of a human disease in which leukocytes are genetically deficient in this family of antigens. Arnaout, M.A., Dana, N., Pitt, J., and Todd, R.F. III., Deficiency of two human leukocyte surface membrane glycoproteins (Mo1 and LFA-1), Fed. p 44: 2664-2670 (1985). The disease is characterized by recurrent severe bacterial infections and deficiencies in adhesion-dependent functions such as phagocytosis, neutrophil spreading on plastic, leukoaggregation, and chemotaxis.

The Mo1 glycoprotein has been of particular interest as it has been shown that this particular structure has the capacity to bind a component of complement termed iC3b, a fragment of the third component of complement. Arnaout, M.A., Todd, R.F. III, Dana, N., Melamed, J., Schlossman, S.F., and Colten, H.R., Inhibition of phagocytosis of complement C3 or IgG-coated particles and of iC3b binding by monoclonal antibodies to a monocyte-granulocyte membrane glycoprotein (Mo1), *J. Clin. Invest.*, 72:171-179 (1983). Also, the Mo1 glycoprotein is critically important in all of the adhesion-dependent phagocyte functions. Different monoclonal antibodies have been shown to inhibit the functions of the Mo1 glycoprotein.

Mo1 is a cell surface glycoprotein present on granulocytes, mononuclear phagocytes and null cells. Todd, R.F. III, Nadler, L.M. and Schlossman, S.F., Antigens on Human Monocytes, *Journal of Immunology*, 126: 1435-1442 (1981). In humans, this molecule consists of two non-covalently linked proteins of 155,000 and 94,000 daltons. Todd, R.F. III, van Agthoven, A., Schlossman, S.F., and Terhorst, C., Structural analysis of differentiation antigens, Mo1 and Mo2 on human monocytes, *Hybridoma*, 1:329-337 (1982). This complex has been shown to mediate cell adhesion to a variety of surfaces including other granulocytes, endothelium, and inert substrates. Genetic deficiencies in these molecules result in recurrent bacterial infections due to the inability of granulocytes to mediate an antimicrobial inflammatory response. Patients who are deficient in these molecules are characterized by an elevated leukocyte count (called "Leukocytosis") and functional defects in phagocyte activity as measured in vitro by reduced or absent aggregation adhesion to substrates, chemotaxis, and phagocytosis of opsonized particles. Activation of granulocytes and monocytes by soluble inflammatory mediators increases expression of these molecules. Todd, R.F. III, Arnaout, M.A., Rosin, R.E., Crowley, C.A., Peters, W.A. and Babior, B.M., The subcellular localization of Mo1 (Mo1a; formerly gp$^{110}$) a surface glycoprotein associated with neutrophil adhesion, *J. Clin. Invest.*, 74:1280-1290 (1984); Arnaout, M.A., Hakim, R.M., Todd, R.F., Dana, N. and Colten, H.R., Increased expression of an adhesion-promotion surface glycoprotein in the granulooytopenia of hemodialysis, *New Engl. J. Med.* 312: 457-462 (1985). Monoclonal antibodies directed against the Mo1 glycoprotein effectively prevent neutrophil aggregation in vitro as well as prevent phagocytosis. In a rat lung model of neutrophis-mediated lung injury (acute respiratory distress syndrome [ARDS]), anti-Mo1 monoclonal antibody significantly inhibited pulmonary endothelial damage produced by activated human neutrophils. Ismail, G., Morganroth, H.L., Todd, R.F. III, and Boxer, L.A., Prevention of pulmonary injury in isolated perfused rat lungs by activated human neutrophils preincubated with anti-Mo1 monoclonal antibody, *Blood*, 69:1167-1174, (1987).

While the inflammatory response of leukocytes is vital to the eradication of invading microorganisms, a substantial and convincing body of evidence indicates that inflammatory phagocytes cause damage to various organs and tissues when these cells are activated in vivo by soluble inflammatory factors that are generated by inciting pathological events. Harlan, J.M., Leukocyte-Endothelial Interactions, *Blood*, 65: 513-525 (1985). The adhesion and spreading of activated neutrophils and mononuclear phagocytes to vascular endothelial cells with the subsequent release of toxio oxidative metabolites and proteases has been implicated in the organ damage observed in diseases, such as, adult respiratory distress syndrome (ARDS; shock lung syndrome), glomerulonephritis, and inflammatory injury occurring after reperfusion of ischemic tissue such as to the heart, bowel, and central nervous system. (Reviewed in Harlan, J.M., ibid.). That the heart muscle or myocardium is vulnerable to the inflammatory response of activated leukocytes has been demonstrated by the outcome of several investigations. These studies have demonstrated that if dogs are depleted of circulating granulocytes with a neutrophil specific antiserum [Romson, J.L. et al., Reduction of the extent of ischemic myocardial injury by neutrophil depletion in the dog, *Circulation*, 67:1016-1023 (1983)] or nitrogen mustard [Mullane, K.M. et al. Role of leukocytes in acute myocardial infarction in anesthetized dogs: Relationship to myocardial salvage by anti-inflammatory drugs, *J. Pharmacal. Exp. Ther.*, 228: 510-522 (1984)] prior to the induction of regional myocardial ischemia and reperfusion, the size of myocardial infarct that results is significantly smaller compared to dogs with normal circulating neutrophil counts. There are a number of other studies that have shown that agents that inhibit neutrophil activation also result in reduced myocardial infarct size. Romson, J.L. et al., The effect of ibuprofen on accumulation of 111-Indium labelled platelets and leukocytes in experimental myocardial infarotion, *Circulation*, 66: 1002-1011 (1982); Bednar, M. et al., Nafazatrom-induced salvage of ischemic myocardium in anesthetized dogs is mediated through inhibition of neutrophil function, *Circ. Res.* 57: 131-141 (1985).

One monoclonal antibody which evidences the capability of inhibiting adhesion-dependent functions but does not affect binding of iC3b is known as MY904. Dana, N., Styrt, B., Griffin, J.D., Todd, R.F. III, Klempner, M.S., and Arnaout, M.A., Two functional domains in the phagocyte membrane glycoprotein Mo1 identified with monoclonal antibodies, *J. Immunol.*, 137: 3259-3263 (1986). Thus, the binding of the monoclonal antibody MY904 to neutrophils could specifically inhibit migration of neutrophils to an area of inflammation or infection. Further, such specific binding of MY904 could inhibit the adhesion and spreading of activated neutrophils reaching such an area and then block the deleterious effects of toxic substances released by the granulocyte.

The method embodying the invention utilizes the specific advantages of the MY904 monoclonal antibody for reducing injury in vivo. The MY904 monoclonal antibody is administered in vivo in the setting of an acute inflammatory response mediated by inflammatory leukocytes, for example, in an acute coronary thrombosis experience just prior to the restoration of myocardial blood flow to ischemic mycocardium. This infusion of MY904 antibody to impact on the phagocyte population in peripheral blood or tissue may inhibit or diminish the ability of these inflammatory cells to migrate to the inflammatory site within the affected tissue; and further, may inhibit adhesion of neutrophils, for instance, in such area so as to inhibit or minimize the potential deleterious effects of toxic substances released by adherent cells. For example, this procedure was determined to materially reduce tissue damage in the area of myocardial infarction after myocardial blood flow is returned.

SUMMARY OF THE INVENTION

The method of materially reducing tissue injury mediated by inflammatory phagocytic leukocytes, such as, but not limited to, myocardial infarct size. The monoclonal antibody MY904 is administered in vivo in anticipation of or early in the course of a potentially injurious inflammatory response mediated by activated phagocytic leukocytes, such as in a myocardial infarct experience, prior to the restoration of myocardial blood flow (interrupted due to an acute coronary thrombosis) by the action of a thrombolytic agent or surgery. The MY904 monoclonal antibody serves to inhibit certain functions of granulocytes and mononuclear phagocytes which ordinarily induce damage of tissue at an inflammatory site, such as in the area of myocardial ischemia with attendant tissue damage after reperfusion. The use of the MY904 monoclonal in the setting of reperfusion myocardia injury is shown to be effective in decreasing the size of anticipated infarction by a significant percentage when administered in vivo prior to reperfusion of ischemic myocardium.

PREFERRED EMBODIMENT OF THE INVENTION

The monoclonal antibody employed in the method of the invention is identified by the designation MY904. It was developed from the fusion of murine spleen cells immunized with human chronic granulocytic leukemia (CGL) cells by standard procedure described by Kohler and Millstein, Nature, 256: 495–49(1975). The granulocytic leukemia cells used in the immunization procedure were obtained from newly diagnosed patients with CGL as part of diagnostic evaluation. Blood was obtained by venipuncture and mononuolear cells separated from granulocytes and red blood cells by Ficoll-Hypaque density gradient sedimentation, 1.077g/cc. The mononuclear cell fraction was composed of immature granulocytes and blast cells. These cells were cryopreserved, and mice immunized at weekly intervals for 4 weeks with $10 \times 10^6$ thawed mononuclear cells injected intraperitoneally. Three days prior to fusion, $10 \times 10^6$ similarly treated CGL mononuclear cells were injected intravenously into the tail vein of the mouse. For the fusion, the spleen was removed and a single cell suspension made of splenocytes. The spleen cells were then mixed with the NS-1 plasmacytoma cell line at a ratio of 8 spleen cells to 1 NS-1 cell in serum free media. The cells were centrifuged to a pellet, suspended in 0.5 ml. of 30 % polyethylene glycol for 8 minutes at 25° C., followed by washing of the cells one time in serum free media and dilution in HAT media prior to distribution of the cells in microtiter plates.

Monoclonal antibody producing hybridoma clones reactive with the immunizing cell population were selected by immunofluorescence screening 14 days after the infusion. Monoclonal antibody MY904 was identified as an antibody which reacted with CGL cells as well as with normal human granulocytes, monocytes, and a fraction of large granular lymphocytes. The monoclonal antibody MY904 reacted with more than 90 % of granulocytes of 10 of 10 patients tested. The monoclonal antibody MY904 does not react with T lymphocytes or B lymphocytes. The monoclonal antibody immunoprecipitates a glycoprotein composed of 2 subunits, 155,000 daltons and 94,000 daltons from surface labelled normal human granulocytes. Dana, N., et al., Two functional domains in the phagocyte membrane glycoprotein Mo1 identified with monoclonal antibodies *J. Immunol.*, 137:3259–3263 (1986). The distribution of reactivity of monoclonal antibody MY904 and the molecular weight of the antigen identified by this monoclonal antibody indioates that the antigen is the CD116/CD18 ("Mo1 ") glycoprotein. Functional studies have further indicated that monoclonal antibody MY904 does not inhibit iC3b binding but is a potent inhibitor of the adhesion-dependent processes, granulocyte spreading on plastic and chemotaxis (Dana et al., Two functional domains in the phagocyte membrane glycoprotein Mo1 identified with monoclonal antibodies, *J. of Immunol.*, 137:3259–3263 (1986). In comparison with other anti-Mo1 monoclonal antibodies, antibody MYg04 was unique in that it inhibited only adhesion-dependent functions but not binding of iC3b. Other antibodies tested include monoclonal antibodies 44, 903, 94, 17, OKM1O, and Leu-15. Dana et al , ibid.

Thus, monoclonal antibody MY904 identifies the Mo1 granulocyte-monocyte cell surface glycoprotein, and further binds specifically to an epitope on that glycoprotein which is involved in adhesion dependent processes of granulocyte/monocyte activities.

A sample of the hybrid cell line capable of producing MY904 monoclonal antibodies is on deposit with the American Type Culture Collection, (A.T.C.C.) and is assigned A.T.C.C. No. HB 9510.

Studies in vitro have shown that human, canine and subhuman primate leukocytes have in common the Mo1 glycoprotein. Letvin, N.L., Todd, R.F. III, Palley, L.S. and Griffin, J.D., Conservation of myeloid surface antigens on primate granulocytes, *Blood.* 61:408–410 (1983). Further, a study was reported wherein a leukocyte glycoprotein deficiency syndrome in a dog was found to be similar to that recognized in a human. Giger, U., Boxer, L.A., Simpson, P.A., Lucchesi, B.R., and Todd, R.F. III, Deficiency of leukocyte surface glycoproteins Mo1 , LFA-1, and Leu M5 in a dog with recurrent bacterial infection, An animal model, *Blood,* 69:1622–1630(1987). The monoclonal antibody MY904 was shown to bind to the alpha subunit (CD11b) of both dog and human leukocytes. Also, binding of the MY904 monoclonal antibody to normal dog neutrophils did effectively inhibit neutrophil aggregation in vitro when stimulated with the phorbol ester PMA (Giger et al., ibid). It is believed that the method embodying the invention which employs in vivo administration of a specified monoclonal antibody to a live human or animal suffering from a phagocyte mediated inflammatory response, such as from induced myocardial ischemic event with attendant reduction in myocardial damage upon subsequent reperfusion of the myocardium is unique and unexpected.

In the example of administering MY904 antibody to attenuate myocardial reperfusion injury, a group of 23 adult dogs was first prepared. The animals were anesthetized and their hearts were exposed through a left thoracotomy in the fifth intercostal space and suspended in a pericardial sling. The left circumflex coronary artery was instrumented with a calibrated electromagnetic flow probe for the continuous recording of blood flow. Catheters were placed into the aorta for blood pressure recording and into the left jugular vein for monoclonal antibody infusion and blood sampling. The standard limb lead 11 electrocardiogram was recorded continuously.

Regional myocardial ischemia was produced by occluding the circumflex artery for ninety (90) minutes and then reperfusing the myocardium in the presence of a critical stenosis or narrowing of a blood vessel. This procedure prevents development of hemorrhagic infarction and reduces the incidence of reperfusion induced ventricular fibrillation. After reperfusing the myocardium for six (6) hours, the heart was electrically fibrillated and excised. The infarct size was assessed as a percentage of the area of the myocardium at risk of infarction as well as percentage to the total left ventricle. The ex vivo dual perfusion histochemical staining technique described in Romson et al., The beneficial effects of oral ibuprotein on coronary artery thrombosis and myocardial ischemia in the conscious dog., *J. Pharm. and Exp. Therap.*, 215:271 (1980), was employed. The cannulated circumflex was perfused with 1.5 % triphenyltetrazolium chloride (TPT) solution buffered with 20 mM potassium phosphate (pH 7.4), while simultaneously perfusing the remainder of the coronary circulation with Evan's blue dye introduced into the aorta. Both solutions were delivered to the respective vascular distributions under a constant pressure of 100 mm Mercury at a temperature of 37° C. for five minutes. The hearts were then cut into 5 or 6 centimeter thick transverse sections and infarct size was determined planimetrically. This accepted method of measuring infarct size accurately demarcates viable from non-viable myocardial tissue a determined by histochemical reaction between TPT and myocardial dehydrogenase enzymes.

With this preparation of the animals completed, two groups of dogs were studied. One group, 11 in number, designated the "controls" group, received 5 % human serum albumin, the vehicle for the monoclonal antibody. The second group of animals, 9 in number, received the pharmaceutic grade monoclonal antibody MY904 in amounts of one (1) mg/kg infused intravenously over a ten (10) minute period (45 minutes) after regional myocardial isohemia was induced (45 minutes prior to reinitiation of coronary blood flow). Detection of binding of the MY904 antibody to the Mo1 antigen of dog leukocytes was monitored. The monoclonal antibody MY904 was supplied by Coulter Immunology Division, Coulter Corporation, in Hialeah, Florida.

At 0, 85 and 120 minutes after injection of MY904 antibody into a dog, 4 ml aliquots of venous blood were withdrawn from experimental subjects, placed into EDTA-containing tubes, and centrifuged for 5 minutes at 800 g. Plasma was separated from the pellet and was saved for subsequent analysis of residual monoolonal antibody. The cellular pellet was depleted of erythrocytes by ammonium chloride lysis, and the residual leukocytes were analyzed for the presence of pre-existing bound anti-Mo1 antibody by immunofluorescence staining. $1 \times 2\text{-}10^6$ leukocytes were incubated for 30 minutes at 4° C. in buffer alone or in buffer containing a saturating concentration of murine anti-Mo1 antibody. The cells were then washed and incubated for an additional 30 minutes at 4° C. in buffer containing a saturating concentration of fluorescein-conjugated goat anti-mouse immunoglobulin. Antibody binding, either as a result of in vivo administration of anti-Mo1 or after in vitro exposure to additional anti-Mo1 antibody, to dog neutrophils and monocytes was assessed by flow cytometry after selective gating on these myeloid cells, as determined by log forward angle versus log right angle light scatter, using an EPICS® C flow cytometer available from Coulter Corporation of Hialeah, Florida. The fluoresoence intensity of 5000 cells per determination was used as a quantitative measure of monoclonal antibody binding.

To document the administration of the MY904 anti-Mo1 monoclonal antibody sufficient to produce anti-Mo1 antibody excess in the plasma or sera of treated dogs, samples of plasma (EDTA-anticoagulated blood) or serum were analyzed. This was assessed by indirect immunofluorescence analysis in which $\times 10^6$ Mo1 -positive test cells, calcium ionophore A23187-stimulated human neutrophils, were incubated in buffer containing dog plasma or serum ($\frac{1}{2}$, $\frac{1}{4}$, $\frac{1}{8}$, 1/16 dilutions) for 30 minutes at 4° C. Then the cells were washed in buffer containing a saturating concentration of fluorescein-conjugated goat anti-mouse immunoglobulin for an additional 30 minutes at 4° C. Monoclonal antibody binding to test cells were quantitated by flow cytometry procedures as described herein using the EPICS® instrument.

To evaluate neutrophil accumulation in myocardial tissue, 50–200 mg samples of myocardium were taken from the central infarct region, the non-infarcted tissue within the area at risk, the endocardial to epicardial border zone between infarct region and area at risk and also from normal non-infarcted and unstained myocardium. Tissue samples were homogenized and assayed for myeloperoxidase content as described in Bradley, P.O., et al., Measurement of cutaneous inflammation: Estimation of neutrophil content with an enzyme marker, *J. Invest. Derm.*, 78: 206–209 (1982). The myeloperoxidase content of myocardial tissue after infarction has been correlated with histologic evidence of neutrophil infiltration as described in Bednar, M., et al., *Circ. Res.*, 57:131–141 (1985); Mullane, K.M., et al., *J. Pharmacological Methods*, 14:157–167 (1946).

To obtain a histological assessment of infarction and neutrophil accumulation within the myocardium, representative histological sections stained with hematoxylin and eosin from each heart were evaluated by an independent qualified investigator who was unaware of the specific treatment. The data was evaluated.

To assess effects of monoclonal antibody on isolated neutrophil aggregation, neutrophils were isolated from venous blood of untreated dogs by Ficoll-hypaque gradient techniques. Red blood cells were lysed with buffered ammonium chloride and resuspended to a concentration of $10^7$ per ml in Hank's balanced salt solution. Aggregation was assessed in a platelet aggregation profiler, Model PAP-3, BIO/DATA Corporation, Horsham, PA. Samples of neutrophils were preincubated with MY904 and negative control antibodies and then activated with 125 mg/ml PMA.

All data were compared to respective control group in which values of $P<0.05$ were considered significant.

As previously noted, twenty-three dogs were started in the study to assess the effects of anti-Mo1 monoclonal antibody on the myocardial infarct size that results after regional isohemia and reperfusion. Of these 23 dogs, 16 were included in the final analysis of infarct sizes. Three dogs were eliminated from the study due to failure to develop objective signs of ischemia as measured by electrocardiographic changes and four dogs, 3 untreated and 1 treated with anti-Mo1 antibody, were eliminated due to ventricular fibrillation.

Mean arterial blood pressure (MAP) heart rate (HR) left circumflex (LCX) blood flow and rate pressure product (RPP;MAP$\times$HR/100) were measured at regular intervals during the experiments to determine whether the antibody had any effects on these parameters. Data accumulated are depicted in FIGS. 1A, 1B, 1C and 1D respectively. The two treatment groups had similar MAP, HR, RPP and LCX blood flow at baseline and at every time point during the experiments. Thus, the protective effects of the antibody could not be attributed to changes in myocardial blood supply, as measured by LCX blood flow, or myocardial oxygen demand as measured by RPP or HR or MAP.

Figure 1A:
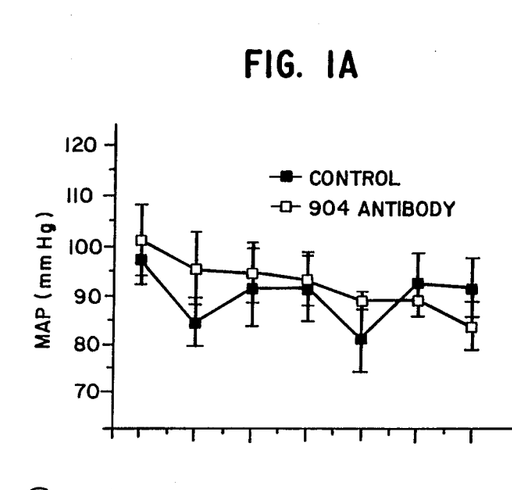
FIG. 1A is a graphic illustration of mean arterial blood pressure (MAP) data accumulated in practicing the method embodying the invention.
Figure 1B:
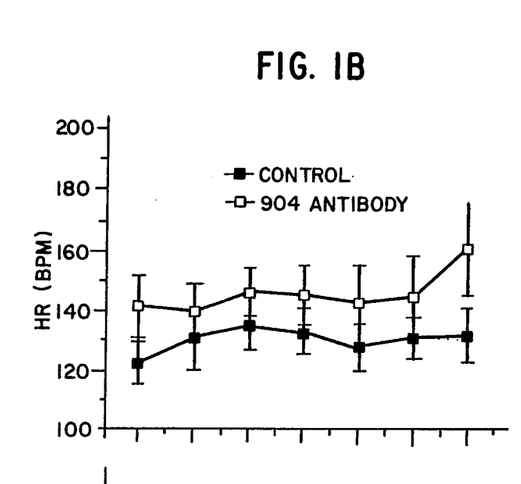
FIG. 1B is a graphic illustration of the heart rate (HR) data accumulated in practicing the said method.
Figure 1C:
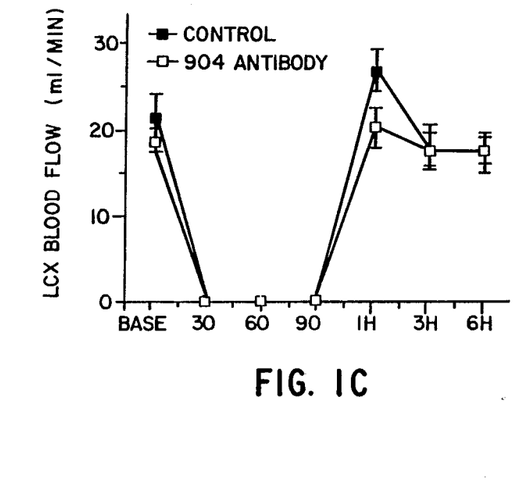
FIG. 1C is a graphic illustration of the left circumflex blood flow (LCX) data accumulated in practicing said method.
Figure 1D:
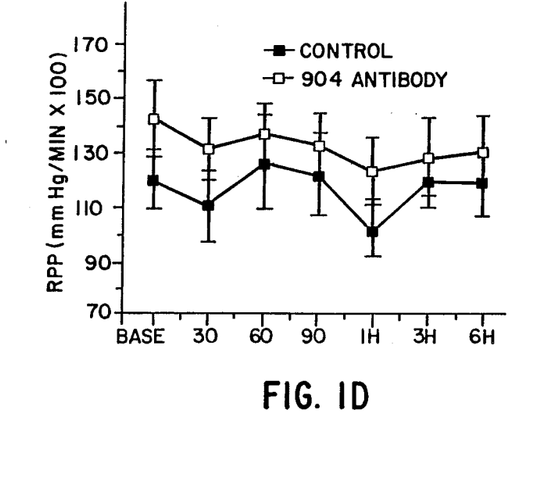
FIG. 1D is a graphic illustration of the rate pressure product (RPP) data accumulated in practicing said method.
Figure 2:
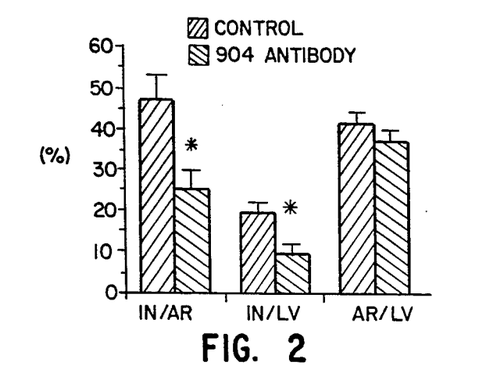
FIG. 2 is a graphic illustration of data accumulated to show the effect of the invention on resulting myocardial infarct size.
Figure 3:
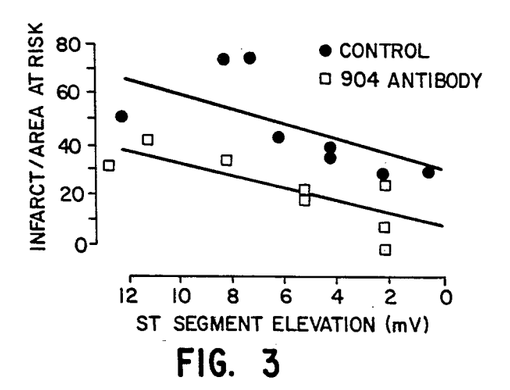
FIG. 3 is a graphic illustration of data accumulated to express infarct size as a function of the extent of the ST segment of an electrocardiogram.

Infarct size was reduced by 46 % by the administration of the anti-Mo1 antibody as compared to control, as seen from the data of FIG. 2. Similarly, infarct size was significantly smaller with monoclonal antibody treatment when infarct size was expressed as a percentage of the total left ventricle. The percentage of the left ventricle that was rendered ischemic, i.e., the area at risk/left ventricle, was similar between treatment groups. When infarct size is expressed as a function of the extent of ST segment elevation on the electrocardiogram, there exists a good correlation with each treatment group describing a different regression line as seen from the data of FIG. 3. These data suggest that for a given severity of myocardial ischemia as measured by ST segment elevation, the infarct size that results is larger in the control group compared to the monoclonal antibody treated group. Thus, myocardial infarct size is reduced by monoclonal antibody treatment independent of the severity of ischemia.

By immunofluorescence analysis, the neutrophils of all 20 experimental subjects expressed the antigenic epitope detectable by the anti-Mo1 MY904 monoclonal antibody. In the 9 dogs who received anti-Mo1 monoclonal antibody at each time point after antibody administration, (i.e., 40, 75, and 405 minutes after antibody administration), the serum or plasma contained residual anti-Mo1 antibody as assayed by immunofluorescence staining of serum or plasma-treated Mo1 positive test cells. This indicated that an infusion of 1 mg/kg was sufficient to produce antibody excess in vivo. Detectable subsaturating amounts of bound antibody were found on the leukocytes of only 6 out of 9 dogs which may reflect antibody dissociation from the membrane prior to assay by incubation with the fluorescein-conjugated goat anti-mouse immunoglobulin reagent.

Figure 4:
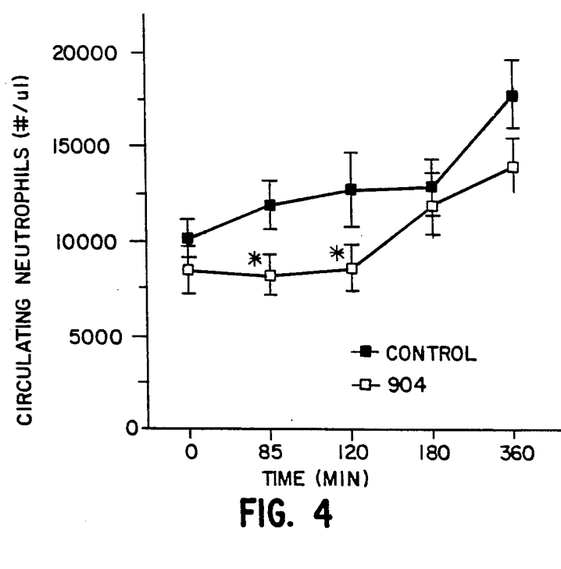
FIG. 4 is a graphic illustration of data accumulated to show circulating neutrophil counts during the myocardial infarction process.

FIG. 4 data shows that neutrophil counts normally increase as seen in the control group during the process of myocardial infarotion. However, treatment with anti-Mo1 antibody suppressed this early rise in circulating neutrophil counts when the two groups are compared. These data, in conjunction with the measurement of excess antibody in the blood and antibody bound to leukocytes, confirm that neutrophils from the antibody treated group are not being cleared from the circulation. One potential problem with the treatment of leukocytes with antibodies is that they may be quickly cleared because of the antibody binding to the cell surfaces. These data suggest that the treatment with this antibody does not cause a drastic reduction in the number of circulating neutrophils.

In an additional study, a third group of five (5) dogs was treated in an identical manner with a negative control murine IgG1 monoclonal antibody, i.e., non-reactive with dog leukocytes. We determined that infarct size after reperfusion was not materially different from that exhibited by the other control group receiving HSA diluent.

The data developed from our method evidenced that prevention of neutrophil adhesion by a monoclonal antibody, MY904, directed against the leukocyte adhesion promotion molecule Mo1 can reduce reperfusion injury in a well characterized animal model of myocardial infarction. The data developed by the method of the invention indicate that administration of the anti-Mo1 monoclonal antibody MYg904 can reduce myocardial infarct size, but not by lessening the severity of the ischemia. Since the duration of ischemia was ninety (90) minutes in all instances, the mechanism of protection by the MY904 antibody is a likely consequence of its effects on neutrophil adhesion with a reduction neutrophil-mediated injury of ischemic myocardium. Heretofore, it was considered that the two major determinants of myocardial infarct size were the severity and duration of the ischemia period.

It will be appreciated from the data accumulated from practicing the method embodying the invention that administering the monoclonal antibody MY904 to a subject within forty five minutes of regional myocardial ischemia materially reduces infarct size independently of the severity of the ischemia. Further, the data shows that inhibition of leukocyte adhesion by anti-Mo1 monoclonal antibody MY904 after occurrence of regional myocardial ischemia results in reduced myocardial reperfusion injury as measured by infarct size. The size of myocardial infarct expressed as a percentage of the area at risk of infarction that resulted was reduced by 46% with the MY904 monoclonal antibody treatment compared to the control.

For treatment of a human experiencing a coronary thrombotic incident using the method embodying the invention, medical experience indicates that a patient who experiences pain or discomfort in his chest would be brought to a hospital usually within thirty to sixty minutes thereafter on an emergency basis. He would be examined promptly to document the occurrence of acute myocardial ischemia and the location of a coronary artery occlusion, and treatment would be prescribed. Such treatment may be that of infusing a thrombolytio agent (e.g. streptokinase or tissue plasminogen activator [TPA]) which might dissolve the blood clot which caused the acute coronary occlusion. Another treatment is surgical in nature where a balloon oatheter is inserted into the circulatory system and directed to the blood clot area for eliminating the brookage. In either manner of treatment, just prior to the intervention resulting in reperfusion of ischemic myocardium (i.e., restoration of coronary artery blood flow), a quantity of MY904 monoclonal antibody is injeoted intravenously into the patient. A single intravenous dose or multiple doses may be administered to optimally attenuate the inflammatory response. The MY904 monoclonal antibody thereafter functions in the manner desoribed herein to reduce tissue damage (infarct size) independently of the severity of the ischemic event. The MY904 monoclonal antibody infusion functions to reduce myocardial reperfusion injury by inhibiting undesired neutrophil functions.

Procedural steps involved in practicing the method embodying the invention may be varied in minor respects without departing from the scope or spirit of the invention as stated in the appended claims.

We claim:

1. A method of treating a human or animal host with the intent of reducing tissue damage occurring at an inflammatory site in any part of the body of a host experiencing a phagocyte-mediated inflammatory condition, said method comprising:

administering in vivo a monoclonal antibody which will bind specifically only to the CD11b part of the CD11/CD18 glycoprotein of the Mo1 antigen expressed on the surface of granulocytes and other phagocytic cells and will inhibit the CD11/CD18 adhesion dependent cellular interactions of such cells reflecting their immonoloical inflammatory response function which contributes to such damage.

2. The method of claim 1 in which said monoclonal antibody binds to an epitope on the CD11b, 155,000 dalton molecular weight peptide molecule of the Mo1 glycoprotein expressed on the surface of such cells.

3. The method of claim 1 in which said inflammatory site is located at the vascular endothelial cell interface or subcellular matrix of a body part.

4. The method of claim 1 in which said inflammatory site is in endothelial tissue of a body part.

5. The method of claim 1 in which said inflammatory site is in a joint of the body part.

6. The method of claim 1 in which said inflammatory site is developed from a myocardial infarct condition.

7. The method of claim 1 in which the monocolonal antibody is administered intravenously at a selected time period prior to or during said inflammatory condition.

8. The method of claim 1 in which said monoclonal antibody binds the Mo1 glycoprotein of neturophils.

9. A method of reducing myocardial inflammation damage in a human patient experiencing acute coronary thrombosis, said patient having been treated initially either medically or surgically to renew myocardial blood flow at the inflammatory site, said method comprising supplying intravenously at least prior to such blood flow renewal a quantity of a murine monoclonal antibody which binds specifically only an epitope expressed on CD11b part of CD11/CD18 glycoprotein of the Mo1 surface antigen of neutrophils whereby to inhibit the adhesive-dependent cellular interactions of the neturophils at said site reflecting their immunological response function whereby to decrease the deleterious action of neturophils at said site.

10. A method of treating a human host with the intent of reducing tissue damage occurring at an inflammatory site in the body of the human experiencing an inflammatory condition, said method comprising:

infusing into the body prior to or during said inflammatory condition a quantity of murine monoclonal antibody which will bind specifically only to an epitope expressed on the CD11b, 155,000 dalton molecular weight peptide of the Mo1 antigen expressed on the surface of neutrophils and will inhibit the CD11/CD18 adhesion dependent intercellular reactions of neturophils reflecting their immunological response function which contributes to such damage.

* * * * *

UNITED STATES PATENT AND TRADEMARK OFFICE
CERTIFICATE OF CORRECTION

PATENT NO. : 4,935,234

DATED : June 19, 1990

INVENTOR(S) : Robert F. Todd III, Benedict R. Lucchesi, Paul J. Simpson, James D. Griffin and Stuart F. Schlossman It is certified that error appears in the above-identified patent and that said Letters Patent is hereby corrected as shown below:

Col. 1, line 39, change "cytoplasmio" to --cytoplasmic--.

Col. 2, line 22, after "Fed." insert --Proc.--.

line 45, change "moleoule" to --molecule--.

line 58, change "Leukocytosis" to --leukocytosis--.

Col. 3, line 3, change "granulooytopenia" to --granulocytopenia--.

line 8, change "neutrophis" to neutrophil --.

line 27, change "toxio" to --toxic--.

line 55, change "infarotion" to --infarction--.

Col. 4, line 43, change "myocardia" to --myocardial--.

Col. 5, line 13, change "mononuolear" to --mononuclear--.

line 52, change "indioates" to --indicates--.

line 62, change "MYg04 to --MY904--.

UNITED STATES PATENT AND TRADEMARK OFFICE
CERTIFICATE OF CORRECTION

PATENT NO. : 4,935,234

DATED : June 19, 1990

INVENTOR(S) : Robert F. Todd III, Benedict R. Lucchesi, Paul J. Simpson, James D. Griffin and Stuart F. Schlossman It is certified that error appears in the above-identified patent and that said Letters Patent is hereby corrected as shown below:

Col. 7, line 6, change "a" to --as--.

line 17, change "isohemia" to --ischemia--.

line 28, change "monoolonal" to --monoclonal--.

line 55, change "x $10^6$" to --1 x $10^6$--.

Col. 8, line 36, change "isohemia" to --ischemia--.

Col. 9, line 52, change "MYg904" to --MY904--.

Col. 10, line 18, change "thrombolytio" to --thrombolytic--.

line 21, change "oatheter" to --catheter--.

line 23, change "brookage" to --blockage--.

line 27, change "injeoted" to --injected--.

UNITED STATES PATENT AND TRADEMARK OFFICE
CERTIFICATE OF CORRECTION

PATENT NO. : 4,935,234

DATED : June 19, 1990

INVENTOR(S) : Robert F. Todd III

It is certified that error appears in the above-identified patent and that said Letters Patent is hereby corrected as shown below:

line 31, change "desoribed" to --described--.

line 53, change "immunoloical" to

--immunological--.

Signed and Sealed this

Twenty-second Day of October, 1991

*Attest:*

HARRY F. MANBECK, JR.

*Attesting Officer*      *Commissioner of Patents and Trademarks*

UNITED STATES PATENT AND TRADEMARK OFFICE
CERTIFICATE OF CORRECTION

PATENT NO. : 4,935,234

DATED : June 19, 1990

INVENTOR(S) : Robert F. Tood III, Benedict R. Lucchesi, Paul J. Simpson, James D. Griffin and Stuart F. Schlossman It is certified that error appears in the above-identified patent and that said Letters Patent is hereby corrected as shown below:

On the title page, at "[73] Assignee:" add the name of assignee
--The University of Michigan, Ann Arbor, Mich.--.

Column 1, after the title insert:

--This invention was made with Government support under National Cancer Institute Grant #CA-39064 and Heart, Lung and Blood Institute Grant #HL-19782-12--.

Signed and Sealed this

Third Day of March, 1992

Attest:

HARRY F. MANBECK, JR.

Attesting Officer

Commissioner of Patents and Trademarks